United States Patent
Leong et al.

(10) Patent No.: US 12,291,495 B2
(45) Date of Patent: May 6, 2025

(54) PROCESS FOR THE PRODUCTION OF SUBSTITUTED 2-[2-(PHENYL)ETHYLAMINO] ALKANEAMIDE DERIVATIVES

(71) Applicant: Newron Pharmaceuticals S.p.A., Bresso (IT)

(72) Inventors: William Leong, Westfield, NJ (US); Dongxiao Lan, Shanghai (CN); Weifang Zhang, Shanghai (CN); Xiang Fang, Shanghai (CN); Sizhong Wu, Shanghai (CN)

(73) Assignee: Newron Pharmaceuticals S.p.A., Bresso (IT)

( * ) Notice: Subject to any disclaimer, the term of this patent is extended or adjusted under 35 U.S.C. 154(b) by 817 days.

(21) Appl. No.: 17/603,019

(22) PCT Filed: Apr. 14, 2020

(86) PCT No.: PCT/EP2020/060470
§ 371 (c)(1),
(2) Date: Oct. 12, 2021

(87) PCT Pub. No.: WO2020/212352
PCT Pub. Date: Oct. 22, 2020

(65) Prior Publication Data
US 2022/0185766 A1    Jun. 16, 2022

(30) Foreign Application Priority Data
Apr. 17, 2019  (EP) .................................... 19169715

(51) Int. Cl.
*C07C 231/14* (2006.01)
*C07B 59/00* (2006.01)
(Continued)

(52) U.S. Cl.
CPC .......... *C07C 231/14* (2013.01); *C07B 59/001* (2013.01); *C07C 41/14* (2013.01);
(Continued)

(58) Field of Classification Search
None
See application file for complete search history.

(56) References Cited

U.S. PATENT DOCUMENTS

| 6,486,202 B1 | 11/2002 | Garcia et al. |
| 2013/0289122 A1* | 10/2013 | Melloni ................. A61P 37/00 |
| | | 564/162 |

FOREIGN PATENT DOCUMENTS

| CN | 101687773 A | 3/2010 |
| JP | 2010529969 A | 9/2010 |

(Continued)

OTHER PUBLICATIONS

Kitade M et al., "Synthesis of 3-O-Acylated epicatechin derivatives via sequential one-pot multi-step reactions", Heterocycles, vol. 73, 2007, pp. 183-186.
Letter reporting office action issued in counterpart Chinese Patent Application on Nov. 6, 2024.
Office Action issued Nov. 6, 2024 in counterpart Chinese Patent Application No. 202080029238.0.
Rosowsky A et al., "Synthesis of new 2,4-diaminopyrido[2,3-d]pyrimidine and 2,4-diaminopyrrolo[2,3-d]pyrimidine inhibitors of Pneumocystis carinii, Toxoplasma gondii, and *Mycobacterium avium* Dihydrofolate Reductase", 2002.
(Continued)

*Primary Examiner* — Sudhakar Katakam
*Assistant Examiner* — Jennifer C Sawyer
(74) *Attorney, Agent, or Firm* — Silvia Salvadori, P.C.; Silvia Salvadori

(57) ABSTRACT

The present invention refers to a process for preparing a compound of formula (I) or a pharmaceutically acceptable salt thereof: wherein R is $(C_3-C_{10})$alkyl, or ω-trifluoro$(C_3-C_{10})$alkyl; $R_1$ and $R_2$ are, independently, hydrogen, hydroxy, $(C_1-C_8)$ alkoxy, $(C_1-C_8)$ alkylthio, halo, trifluoromethyl or 2,2,2-trifluoroethyl; or one of $R_1$ and $R_2$ is in ortho position to the R—O— group and, taken together with the same R—O—, represents a Formula (A) group where $R_0$ is $(C_2-C_9)$alkyl; $R_3$ and $R_4$ are, independently, hydrogen, $(C_1-C_4)$alkyl; or $R_4$ is hydrogen and $R_5$ is a group selected from —$CH_2$—OH, —$CH_2$—O—$(C_1-C_6)$alkyl, —$CH(CH_3)$—OH, —$(CH_2)_2$—S—$CH_3$, benzyl and 4-hydroxybenzyl; or $R_4$ and $R_5$, taken together with the adjacent carbon atom, form a $(C_3-C_6)$cycloalkyl residue; $R_5$ and $R_6$ are independently hydrogen or $(C_1-C_6)$alkyl; or taken together with the adjacent nitrogen atom form a 5-6 membered monocyclic saturated heterocycle, optionally containing one additional heteroatom chosen among —O—, —S— and —$NR_7$— where $R_7$ is hydrogen or $(C_1-C_6)$ alkyl; and wherein optionally one or more hydrogen atom in the groups R, $R_1$, $R_2$, $R_3$, $R_4$, $R_5$ and $R_6$, preferably in the R group, can be substituted by a deuterium atom.

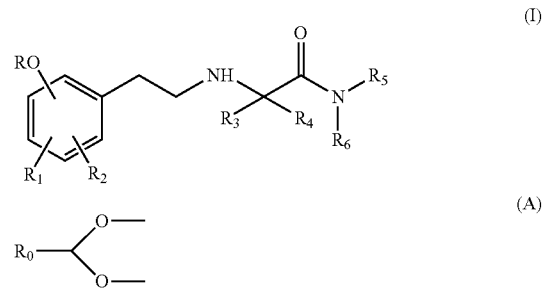

20 Claims, 1 Drawing Sheet

(51) Int. Cl.
*C07C 41/14* (2006.01)
*C07C 45/64* (2006.01)
*C07C 231/12* (2006.01)

(52) U.S. Cl.
CPC ............ *C07C 45/64* (2013.01); *C07C 231/12* (2013.01); *C07B 2200/05* (2013.01)

(56) References Cited

FOREIGN PATENT DOCUMENTS

| | | |
|---|---|---|
| JP | 2015529651 A | 10/2015 |
| JP | 2018043951 A | 3/2018 |
| WO | 2007071311 A1 | 6/2007 |
| WO | 2008151702 A1 | 12/2008 |
| WO | 2013133419 A1 | 9/2013 |

OTHER PUBLICATIONS

Treu M et al., "4a,5,9, 10, 11, 12-Hexahydro-6H-benzo[a[cyclohepta[hi]benzofuran-synthesis of unnatural galantamine analogs", Molecules 2002, 7, 374-381.

Baltj M. et al., "Preparation of vinyl ethers using a witting approach, and their subsequent hydrogenation employing continuous-flow processing" Tetrahedron Letters, Elsevier Amsterdam, NL, vol. 57, No. 16, Mar. 12, 2016, pp. 1804-1806.

Jamison J. et al., "Syntheses and antifungal activity of pseudomycin side-chain analogues. Part 1", Bioorganic & Medicinal Chemistry Letters, Pergamon Amsterdam, NL, vol. 10, No. 18, Sep. 1, 2000, pp. 2101-2105.

Search Report and Written Opinion of PCT/EP2020/060470 of Jul. 23, 2020.

Letter dated Apr. 14, 2020 replying to the Search Opinion established by the EPO.

Office Action issued by Singapore Patent Office in relation to counterpart patent application No. 11202111376P on May 10, 2023.

Jamison J et al., "Syntheses and antifungal activity of Pseudomycin side-chain analogues. Part 1", Bioorganic & Medicinal Chemistry Letters 10 (2000) 2101-2105.

Office Action issued on Feb. 6, 2024 in connection with counterpart Japanese Application No. 2021-560991.

Kobayashi J et al., "Synthesis and optimization of novel alpha-phenylglycinamides as selective TRPM8 antagonists", Bioorganic & Medicinal Chemistry 25 (2017) 727-742.

Office Action issued Dec. 13, 2023 in counterpart Chinese Patent Application No. 202080029238.0.

\* cited by examiner

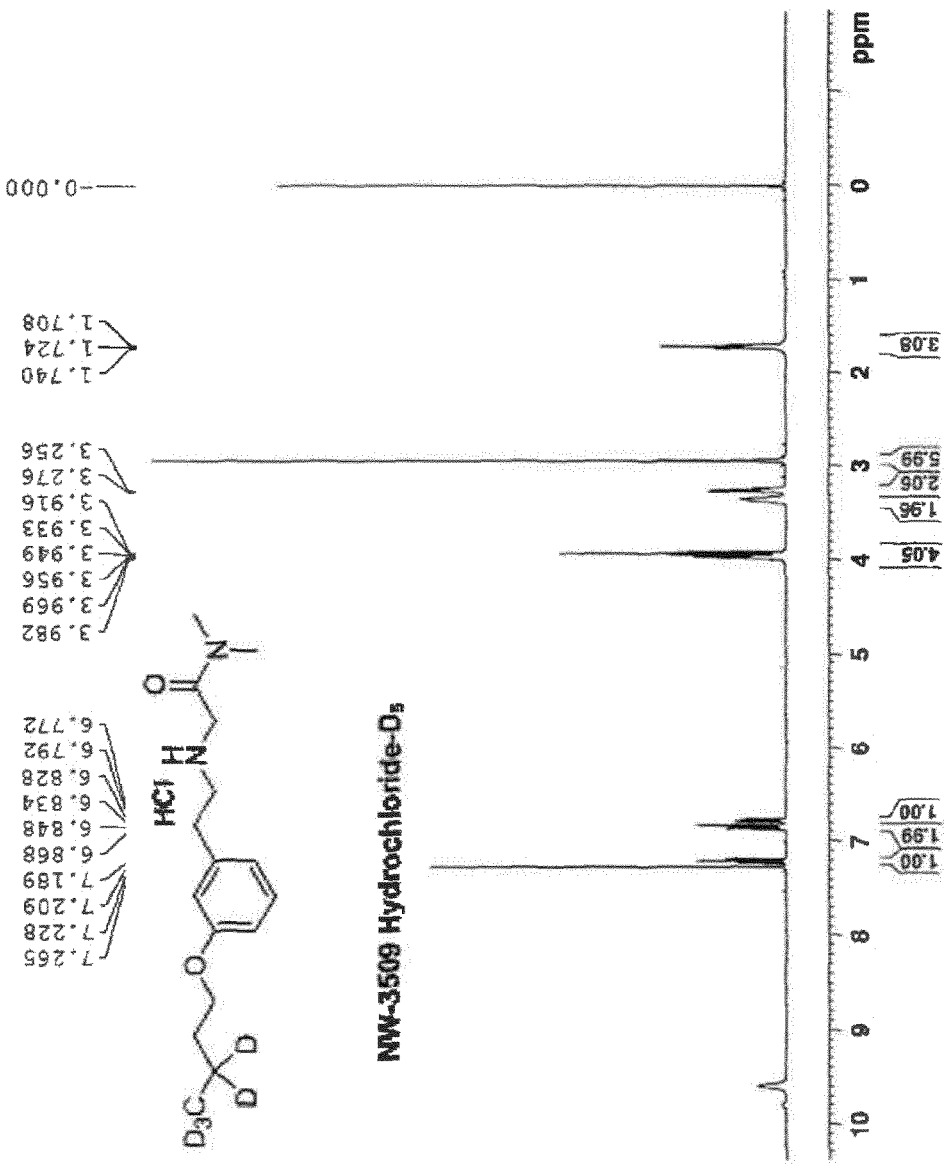

PROCESS FOR THE PRODUCTION OF SUBSTITUTED 2-[2-(PHENYL)ETHYLAMINO] ALKANEAMIDE DERIVATIVES

This application is a U.S. national stage of PCT/EP2020/060470 filed on 14 Apr. 2020, which claims priority to and the benefit of European Application No. 19169715.0filed on 17 Apr. 2019, the contents of which are incorporated herein by reference in their entireties.

The present invention relates to a process for the production of substituted 2-[2-(phenyl)ethylamino]alkaneamide derivatives, in particular 2-[2-(3-butoxyphenyl)-ethylamino]-N,N-dimethylacetamide in high yields with very high chemical purity.

Substituted 2-[2-(phenyl) ethylamino]alkaneamide derivatives, disclosed in WO2008/151702, are sodium and/or calcium channel modulators and therefore are useful in preventing, alleviating and curing a wide range of pathologies where said mechanisms play a pathological role, such as neurological, cognitive, psychiatric, inflammatory, urogenital and gastrointestinal diseases. These compounds are also described to be substantially free of monoamine oxidase (MAO) inhibitory effect.

A new class of fluorinated arylalkylamino carboxamide derivatives which are highly potent as sodium and/or calcium channel modulator are disclosed in WO 2013/000651.

WO 2008/151702 discloses in the examples the synthesis of 2-[2-(3-butoxyphenyl)-ethylamino]-N,N-dimethylacetamide hydrochloride, as summarized in the following Scheme 1:

Scheme 1

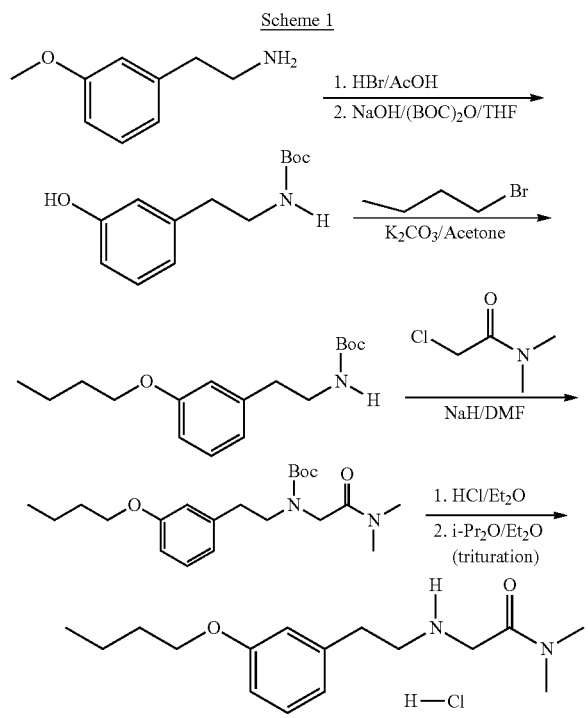

The disclosed process suffers of many drawbacks which make it not scalable at an industrial level:
non commercially available starting material such as 3-methoxyphenylethyl amine, which preparation from commercially available reagents involves a couple of steps;
difficult purifications of intermediates as they are oils;
use of toxic reagents in large excess, such as 1-bromobutane and 2-chloro-N,N-dimethylacetamide, which is potentially genotoxic;
use of non-standard equipment (NaH/DMF is a potentially explosive compound as H2 is generated in the reaction);
non practical and potentially very dangerous conditions for producing the final hydrochloride due to the use of ethereal solvents which easily form peroxides in the presence of air;
low overall yields (about 13%);
unknown purity of the final product.

WO 2008/151702 suggests also alternative methods for preparing 2-[2-(3-butoxyphenyl)-ethylamino]-N,N-dimethylacetamide among which it is suggested to submit an aldehyde to a reductive amination with an α-aminoalkaneamide (p. 20, l. 1-10). The document does not give the conditions and the yield of the reaction and it does not disclose how to prepare the starting aldehyde.

The present inventors have found that 3-butoxyphenylacetaldehyde which is the aldheyde to be used in the reductive amination with an α-aminoalkaneamide to produce 2-[2-(3-butoxyphenyl)-ethylamino]-N,N-dimethylacetamide is high unstable and this makes its use in a large-scale industrial process problematic.

It has now been found an innovative and practical process for manufacturing 2-[2-(phenyl) ethylamino] alkaneamide derivatives, in particular 2-[2-(3-butoxyphenyl)-ethylamino]-N,N-dimethylacetamide, which allows to obtain the final product in high yield and purity.

The process uses easily accessible starting materials and reagents and can be performed in a standard equipment known in the art. Furthermore the process can be carried out step by step or as a sequential telescopic synthesis which allows to save time and resources.

All these characteristics makes the process useful for the industrial production of the active principle.

The present invention relates to a process for preparing a compound of formula (I) or a pharmaceutically acceptable salt thereof:

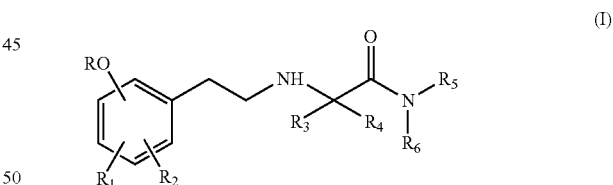

(I)

wherein R is $(C_3-C_{10})$alkyl, or ω-trifluoro$(C_3-C_{10})$alkyl;
$R_1$ and $R_2$ are, independently, hydrogen, hydroxy, $(C_1-C_8)$alkoxy, $(C_1-C_8)$ alkylthio, halo, trifluoromethyl or 2,2,2-trifluoroethyl; or one of $R_1$ and $R_2$ is in ortho position to the R—O— group and, taken together with the same R—O—, represents a

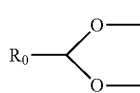

group where $R^0$ is $(C_2-C_9)$alkyl;
$R_3$ and $R_4$ are, independently, hydrogen, $(C_1-C_4)$alkyl; or $R_4$ is hydrogen and $R_5$ is a group selected from —CH$_2$—OH, —$CH_2$—O—($C_1$-$C_6$)alkyl, —$CH(CH_3)$—OH, —$(CH_2)_2$—S—$CH_3$, benzyl and 4-hydroxybenzyl; or $R_4$ and $R_5$, taken together with the adjacent carbon atom, form a ($C_3$-$C_6$) cycloalkyl residue;

$R_5$ and $R_6$ are independently hydrogen or ($C_1$-$C_6$)alkyl; or taken together with the adjacent nitrogen atom form a 5-6 membered monocyclic saturated heterocycle, optionally containing one additional heteroatom chosen among —O—, —S— and —$NR_7$— where $R_7$ is hydrogen or ($C_1$-$C_6$) alkyl;

and wherein optionally one or more hydrogen atom in the groups R, $R_1$, $R_2$, $R_3$, $R_4$, $R_5$ and $R_6$, preferably in the R group, can be substituted by a deuterium atom;

said process comprising the steps of:

a) reacting a compound of formula II):

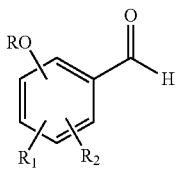

(II)

wherein R, $R_1$ and $R_2$ are as above defined with a compound of formula (III):

(III)

wherein $R_9$ is aryl, preferably phenyl, tolyl, or a (C1-C6) alkyl, preferably methyl, ethyl or n-propyl;

X is Cl, Br or I, preferably Cl and Br;

$R_8$ is ($C_1$-$C_6$) alkyl, preferably methyl, ethyl or n-propyl or aryl, preferably phenyl or tolyl; in the presence of a strong base to obtain a compound of formula (IV):

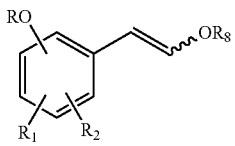

(IV)

wherein R, $R_1$, $R_2$ and $R_8$ are as above defined and b) optionally hydrolyzing the obtained compound of formula (IV) to obtain a compound of formula (V):

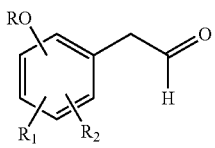

(V)

wherein R, $R_1$ and $R_2$ are as above defined and c) reacting the obtained compound of formula (V) with a compound of formula (VI) or a salt thereof.

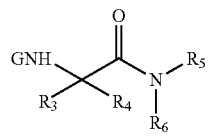

(VI)

wherein $R_3$, $R_4$, $R_5$ and $R_6$ are as above defined and G is hydrogen or a protecting group of the amino group, to obtain a condensation compound;

d) reducing the obtained condensation compound to obtain the compound of formula (I)

or alternatively c') directly reacting the compound of formula (IV) as above defined with the compound of formula (VI) as above defined and reducing the obtained condensation compound to obtain the compound of formula (I); and e) optionally converting the obtained compound of formula (I) into a pharmaceutically acceptable salt thereof.

The condensation compound obtained in step c) may be a Schiff base of the following formula (VII) as diastereoisomer E or Z or a mixture thereof

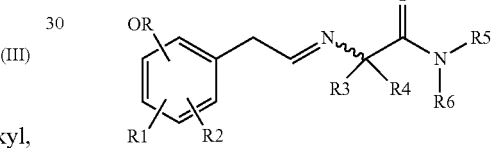

(VII)

or the structurally related alpha-hydroxy-amine of formula (VII$^a$)

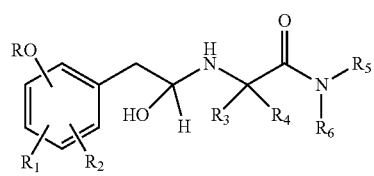

(VII$^a$)

or an unsaturated amine of formula (VII$^b$)

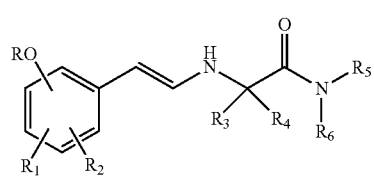

(VII$^b$)

or a salt thereof or a mixture of the above reported condensation compounds.

The condensation of the product of formula (V) with the product of formula (VI) in the presence of aqueous HCl may occur under equilibrium reaction conditions as per the following scheme:

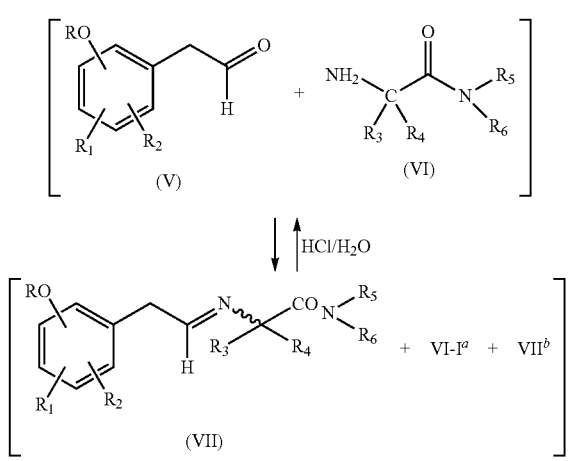

Preferably the condensation compounds, i.e. the Schiff base of formula (VII) and the structurally related condensation compounds of formula (VII$^a$) or (VII$^b$) are not separated from either the starting materials (V) and (VI) or from $H_2O$ in view of to the reduction subsequent step. The strong base of step a) is preferably selected in the group consisting of alkyl lithium, such as butyllithium, lithium hexamethylsilazide, lithium isopropylamide, potassium tert-butoxide. Most preferably the strong base is lithium hexamethylsilazide which can be obtained in situ from hexamethyldisilazane.

In step a) a phosphine of formula $(R_9)_3P$, wherein $R_9$ is as defined above, is formed as side-product. Said phosphine may be oxidized for example by addition of $H_2O_2$ to $(R_9)_3$PO and removed from the reaction mixture, for example by simple filtration.

The product (IV) obtained in step a) is preferably purified by chromatography.

The group G is preferably hydrogen.

Protecting groups of the amino group are reported in Protective Groups in Organic Synthesis-Third Edition Theodora W. Greene and Peter G. M. Wuts, John Wiley & Sons, Inc. 1999 pages 503-550.

Preferably the amino protecting group is a carbamate N-carboxy alkyl group, N-t-butyl carbamate (BOC), N-benzyl carbamate (Cbz), bromobenzyl carbamate, p-chlorobenzylcarbamate, 9-fluorenylmethyl carbamate (Fmoc).

The intermediate products (V) obtained in step b) and the condensation products obtained in step c) may not be isolated and directly used in the next stage of synthesis.

This type of process is known as telescopic process, i.e. a concatenation or through-process, wherein the product of a reaction is carried without isolation into the next step.

The process of the invention is reported in the following Scheme 2:

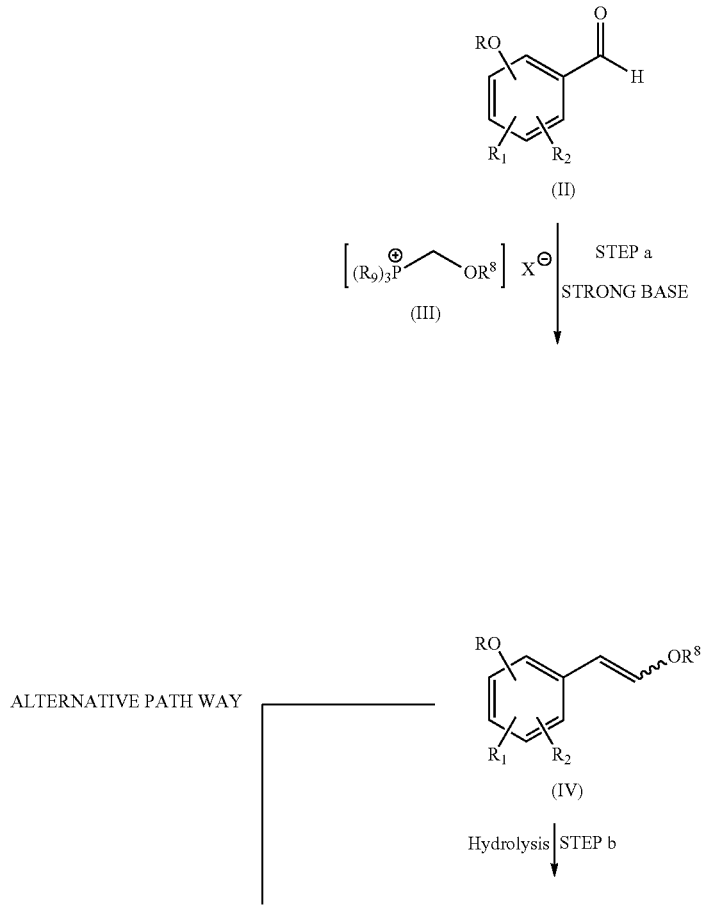

-continued

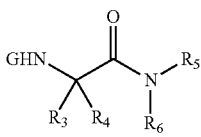
(VI)

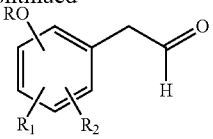
(V)

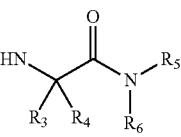
(VI)

STEP c′ | REDUCING AGENT

STEP c

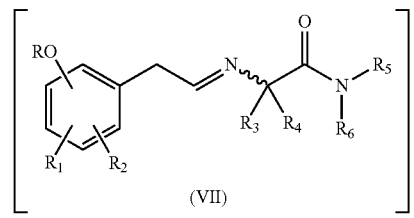
(VII)

STEP d

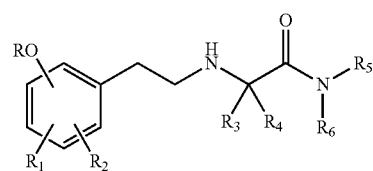
(I)

STEP e | ACID

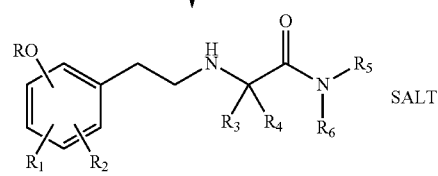
SALT

A preferred process of the invention is the above described process for obtaining a compound of formula (I′):

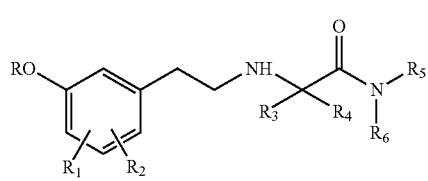
(I′)

wherein R, $R_1$, $R_2$, $R_3$, $R_4$, $R_5$ and $R_6$ are as defined above and the compound of formula (II) has the following formula (II′):

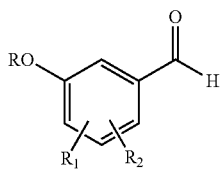
(II′)

wherein R, $R_1$ and $R_2$ are as above defined;

the compound of formula (IV) has the following formula (IV′):

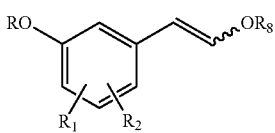

wherein R, $R_1$, $R_2$ and $R_8$ are as above defined; and
the compound of formula (V) has the following formula (V'):

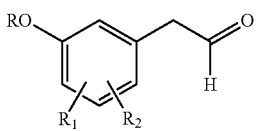

wherein R, $R_1$, and $R_2$ are as above defined.

In said process the condensation compound obtained in step c) is a Schiff base of the following formula (VII') as diastereoisomer E or Z:

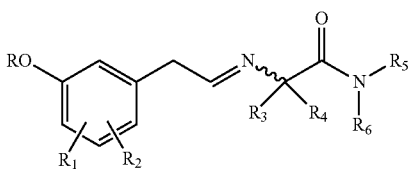

or the structurally related compounds of formula (VII'$^a$) or (VII'$^b$):

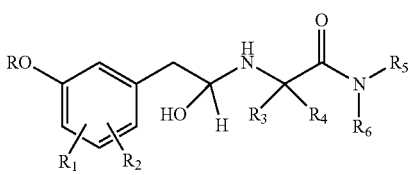

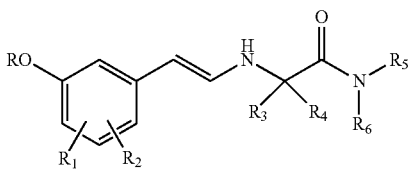

or a salt thereof or a mixture of the above reported condensation compounds.

Preferably the condensation compounds, i.e. the Schiff base of formula (VII') or the structurally related condensation compounds of formula VII'a or VII'b, are not isolated in the present process.

A preferred process of the invention is the above described process for obtaining a compound of formula (I) or (I') wherein:

R is $(C_4-C_6)$alkyl or $CD_3-CD_2-(C_2-C_4)$alkyl;
$R_1$ and $R_2$ are, independently, hydrogen or halo, preferably fluoro;
$R_3$ and $R_4$ are both hydrogen; and
$R_5$ and $R_6$ are, independently, hydrogen or $(C_1-C_3)$alkyl.

A most preferred process of the invention is the above defined process for obtaining a compound of formula (I) or (I') as above defined wherein R is n-butyl or $CD_3-CD_2-CH_2-CH_2-$ and $R_1$, $R_2$, $R_3$, $R_4$, $R_5$ and $R_6$ are hydrogen.

Step a) of the above defined process is a Wittig reaction. The reaction is preferably carried out in polar solvents such as tetrahydrofuran or 2-methyltetrahydrofuran in the presence of a strong base such as alkyllithium, for example butyllithium, lithium isopropylamide, potassium t-butoxide or lithium hexamethyldisilazide (LiHMDS) which can be obtained in situ from hexamethyldisilazane. Lithium hexamethyldisilazide (LiHMDS) is the preferred strong base. The reaction temperature can vary from −20° C. to +25° C. Preferably the reaction is carried out at 0° C. The reaction conditions used in the Wittig reaction are described in Modern Carbonylation Olefination, Edited by Takeshi Takeda 2004 Wiley-VCH, Chapt 1; March's Advanced Organic Chemistry Seventh Edition 2013 by John Wiley and Sons Inc, p. 1165-1167; Synthesis 2003, No. 3, p. 317-334).

Preferably, the phosphine of formula $(R_9)_3$P, wherein $R_9$ is as defined above, formed as side side-product is oxidized for example by addition of $H_2O_2$ to $(R_9)3$ PO and removed, for example by filtration.

Step b) of the above defined process is a hydrolysis reaction which can be carried out in a polar solvent such as acetonitrile, tetrahydrofuran or 2-methyltetrahydrofuran, ethanol, methanol, 1-butanol, methyl tetrabutyl ether (MTBE) or ethyl acetate or a mixture thereof under anhydrous or aqueous acidic conditions. Preferably step b) is carried out under aqueous acidic conditions in the presence of an aqueous acid such as hydrochloric acid, hydrobromic acid, aqueous formic acid, aqueous sulfuric acid, aqueous phosphoric acid, methanesulphonic acid at a temperature ranging from 0° C. to 5° C. Preferably step b) is carried out in acetonitrile and aqueous hydrochloric acid. The aryl acetaldehyde (V) has unexpectedly shown a sufficient stability in aqueous acidic conditions to be productively used in the subsequent step c). Preferably the aryl acetaldehyde (V) in acetonitrile and aqueous hydrochloric acid obtained in step b) is directly used in step c).

Step c) is a condensation reaction which can be carried out in a polar solvent such as acetonitrile, tetrahydrofuran or 2-methyltetrahydrofuran or a mixture thereof in the presence of an aqueous acid such as hydrochloric acid, hydrobromic acid, sulfuric acid, methanesulphonic acid, at a temperature from 0° to 40° C. Contrary to the most common methods used for the preparation of Schiff bases from aldehydes and primary amines that involve azeotropically removing water or the use of a drying agent such as molecular sieves, the condensation reaction of step c) is successfully carried out in the presence of water. Preferably the step c) is carried out in acetonitrile and aqueous hydrochloric acid. Preferably the condensation product obtained in step b) is directly used in step c).

Step d) of the above defined process is a reduction reaction which can be carried out using a reducing agent such as sodium borohydride, sodium triacetoxyborohydride (STAB-H), Pd/$H_2$, $NaBH_3CN$, preferably sodium triacetoxyborohydride (STAB-H), in solvents such as 1,2-dichloroethane, tetrahydrofuran or 2-methyltetrahydrofuran, acetonitrile and N,N-dimethylformamide, ethanol, isopropanol N,N-dimethylacetamide or a mixture thereof at −25° C.+25° C. as described for example in Organic Process Research & Development 2006, 10, 971-1031.

Preferably the reduction is carried out using sodium triacetoxyborohydride (STAB-H) as reducing agent in aqueous acidic conditions such as aqueous acetonitrile and hydrochloric acid.

Step b), Step c) and Step d), can be carried out without isolating the reaction products.

Step e) is an optional salification of the compound of formula (I) with a pharmaceutically acceptable acid such as hydrochloric acid, hydrobromic acid, methanesulphonic acid, paratoluenesulfonic acid, phosphoric acid and oxalic acid. The salification step is preferably carried out in a polar solvent such as methyl tert-butyl ether, methyl isobutyl ketone or a mixture thereof at a temperature ranging from 0° C. to 25° C. The obtained salt has a low solubility in the used solvents and can be isolated as a pure product by filtration.

Preferably the hydrochloric acid salt of a compound of formula (I) is obtained by adding concentrated aqueous HCl (such as 37% aqueous HCl) to the compound of formula (I) dissolved in methyl isobutyl ketone and following azeotropic distillation.

Step c') can be carried out by adding an aqueous acid to a solution of the amine of formula (VI), or a salt thereof such as hydrochloride or hydrobromide, and of the compound of formula (IV) at a temperature from −10° C. to 50° C., followed by the addition of the reducing agent at a temperature from −25 to +25° C. Suitable solvents are either polar protic solvents (methanol, ethanol, isopropanol) or aprotic polar solvents (methylene chloride, tetrahydrofuran, 2-methyltetrahydrofuran, diethylether, methyl isopropyl ether) or mixtures thereof. The reducing agent is selected among sodium triacetoxyborohydride (STAB-H), Pd/$H_2$ and $NaBH_3CN$. Preferably step c') is carried out in THF using acetic acid as aqueous acid sodium triacetoxyborohydride (STAB-H) as reducing agent.

The compound of formula (II) wherein R is as above defined can be obtained by alkylation of a compound of formula (II) wherein R═H with a compound of formula RY wherein R is as above defined and Y a is good leaving group such chloride, bromide, mesylate, para-toluenesulphonate, brosylate, nosylate and phosphate. Preferably Y is chloride.

The above reported alkylation reaction can be carried out in polar organic solvents such as N,N-dimethylformamide, N-methylpyrrolidone, tetrahydrofuran, 2-methyltetrafydrofuran, methyl tert-butyl ether (MTBE), isopropyl acetate, acetonitrile, dimethylsulfoxide, acetone in presence of a suitable base such as KOH, NaOH, $K_2CO_3$, $Et_3N$ or in a biphasic system with the organic solvent (toluene) and water in the presence of a phase transfer catalyst (PTC) such as tetrabutyl ammonium chloride for a time ranging from less than one hour to several hours.

Preferably the alkylation reaction is carried out in N,N-dimethylformamide in the presence of $K_2CO_3$.

The compounds of formula (II) as above defined are commercially available or can be prepared by reactions known in the art.

The compound of formula (III), used in Step a) can be prepared in situ reacting a compound of formula (IX):

$$XCH_2OR_8 \quad (IX)$$

wherein X is as defined above with a compound of formula (X):

$$(R_9)_3P \quad (X)$$

wherein $R_9$ is as defined above in polar solvents such as isopropylmethyl ether, tetrahydrofuran or 2-methyltetrahydrofuran and then preferably reacted in situ with the compound of formula (II) in the presence of a base.

The compound of formula (VI) is a commercially available product or can be prepared by methods known in the art.

The compound of formula (VIII) can be can be prepared by reactions known in the art.

The above reported process is very flexible because step b), c) and d) can be carried out step by step or in a single pot (alternative step c') or in telescopic way, i.e. a process wherein step b), step c) and step d) are carried out without isolating the intermediate products.

"Telescoping" means the execution of multiple transformations (step b, step c and step d) (including quenches and other work-up operations) without isolation of the intermediates. The solutions of the intermediates can be extracted, filtered (as long as the product remains in the filtrate) and the solvent exchanged, but the intermediate is ultimately held in solution and carried forward to the subsequent transformation.

The telescoping process applied to the three steps b), c) and d) of the invention is quite unique, as until the end of step d), where product isolation is carried out, any extraction or work-up is avoided, reagents are added to the reaction mixture and the reaction can be carried out in the same reactor.

The absence of any work-up, any extraction and any crystallization makes this telescopic approach very convenient under an industrial point of view.

In the innovative telescopic process the aldehyde (V) is preferably produced under acidic aqueous conditions. The compound of formula (VI) is added to the reaction mixture in order to run the condensation step. Then the reduction step is carried out by adding the selected reducing agent to the previous condensation aqueous reaction mixture. Only one reaction work-up, for the three steps process, is carried out after the completion of the third step in order to isolate the final solid product (I).

EXPERIMENTAL PART

Example 1

Synthesis of 3-butoxybenzyaldehyde

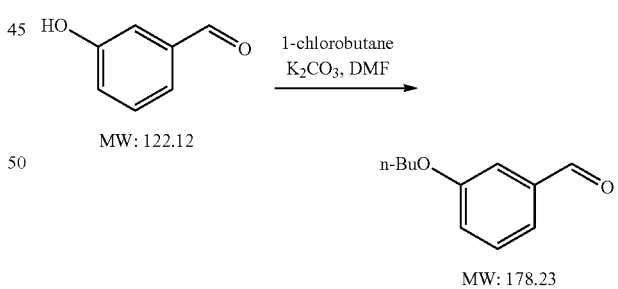

A solution containing 3-hydroxybenzaldehyde 25 kg (204.7 mol), potassium carbonate 39.5 kg (285.8 mol), and 1-chlorobutane 28.5 kg (307.8 mol) in N,N-dimethylformamide 120 kg was heated to 115° C. and kept at this temperature until reaction completion (3-hydroxybenzaldehyde less than 1%). The mixture was cooled, diluted with water 325 kg and then concentrated under vacuum to about 325 L. The batch was diluted with water 126 kg and methyl tert-butyl ether 150 kg was added at about 20° C. The aqueous layer was discarded and the batch was washed sequentially with dilute sodium chloride solution and then water. The batch was concentrated under vacuum and residual methyl tert-butyl ether was replaced by tetrahydrofuran through a series of dilution and concentration under vacuum. The resulting tetrahydrofuran solution containing 33.5 kg (188.0 mol) (91% molar yield, purity 99.7%) of 3-butoxybenzaldehyde was used in the next step.

MS (M+1: 179.1); $^1$H NMR is consistent with the given structure.

Example 2

Synthesis of 3-butoxybenzyaldehyde

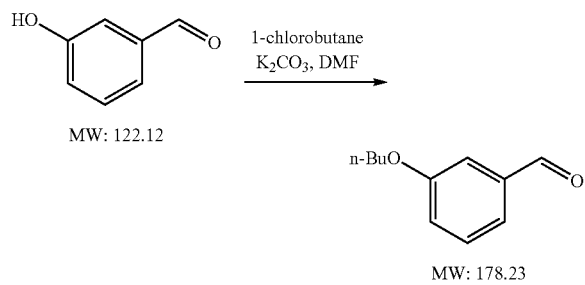

A mixture containing 3-hydroxybenzaldehyde 3.95 kg (32.34 mol), 1-chlorobutane 4.49 kg (48.52 mol), and potassium carbonate 6.26 kg (45.28 mol) in N,N-dimethylformamide 19.75 L was heated to 115-118° C. and kept at this temperature until the reaction was complete (3-hydroxybenzaldehyde circa 0.1% area %). The reaction mixture was cooled to circa 20° C. The slurry was added with a mixture of tert-butyl methyl ether 32.4 L and water 52.9 L and stirred for 15 min. The two phases mixture was allowed to separate. The organic solution was washed with a sodium chloride aqueous solution. The batch was concentrated under reduced pressure at <50° C. to provide the oily product 3-butoxybenzaldehyde 5.57 kg in 96.6% molar yield.

Example 3

Synthesis of 1-Butoxy-3-(2-methoxyvinyl)benzene

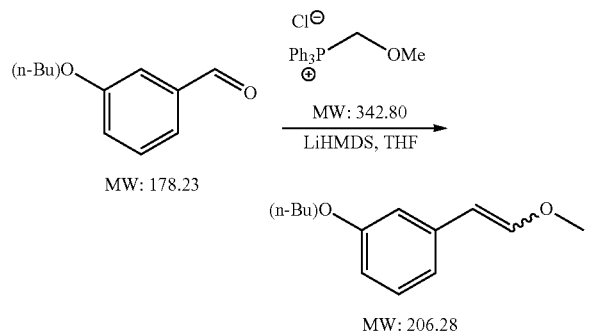

A solution of lithium hexamethylsilazide (prepared from hexamethyldisilazane 53.4 kg (331 mol), n-butyl lithium (2.5 M) in N-Hexane 91 kg (328 mol) in tetrahydrofuran 83 kg at −25° C. to 0° C., was added to a solution of (methoxymethyl)triphenylphosphonium chloride 95.6 kg (279 mol) and tetrahydrofuran 290 kg at about −25° C. A pre-cooled tetrahydrofuran solution of 3-butoxybenzaldehyde 33.5 kg (188 mol) in THF solution, prepared in the previous step, was added and the batch was kept at about 0° C. until complete reaction. The reaction mixture was quenched with water 166 kg (pre-cooled to about 0° C.). The biphasic mixture was concentrated under vacuum to about 266 L. The batch was diluted with n-heptane 77 kg and filtered through Celite with a n-heptane rinse. The combined filtrate was allowed to settle, the aqueous layer was separated and extracted with n-heptane 115 kg. The combined organic layer was washed three times with water 166 kg each time. A solution containing hydrogen peroxide 6.05 kg in water 33 kg was added to the batch and stirred at about 20° C. for about 6 h. The batch was diluted with water 66 kg and then filtered through Celite with a n-heptane rinse. The combined filtrate was allowed to settle and the aqueous layer was discarded. The organic solution was washed three times with water, 100 kg each time. The solution was concentrated to about 66 L and purified on silica gel 160 kg; (200-300 mesh) using n-heptane as the eluent. Fractions containing the product were combined and concentrated under vacuum to about 66 L. The concentrated solution of E and Z 1-Butoxy-3-(2-methoxyvinyl)benzene 25 kg (121.2 mol), 64% molar yield, was used directly in the next step. MS (M+1: 207.2) and $^1$H NMR (DMSO-$d_6$) showed that it is a mixture of E- and Z-isomers. Based on the NMR integration, the ratio is 43:57 of the E:Z isomers.

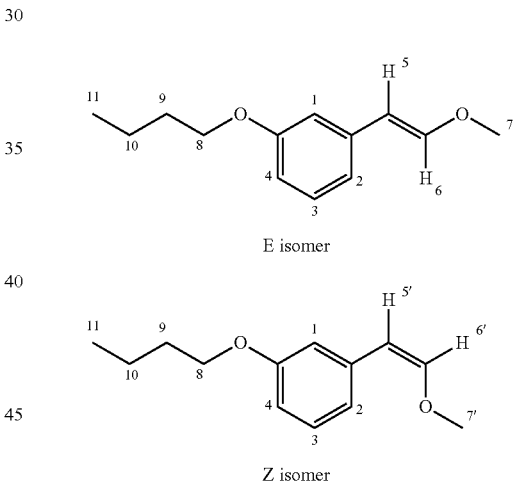

The $^1$H NMR (400 MHz) assignments are tabulated as below:

| Position | $\delta_H$ (ppm) |
| --- | --- |
| 1, 2, 3, 4 | 7.22-6.96 (m, 2H), 6.89-6.74 (m, 1H), 6.73-6.57 (m, 1H) |
| 5' & 5 | 5.79 (d, J = 13.0 Hz, 0.57H) & 5.18 (d, J = 7.1 Hz, 0.43H) |
| 6' & 6 | δ 7.28 (d, J = 13.0 Hz, 0.57H) & 6.28 (d, J = 7.0 Hz, 0.43H) |
| 7' & 7 | 3.85-3.68 (m, 1.29H), 3.65-3.51 (m, 1.71H) |
| 8 | 4.10-3.85 (m, 2H) |
| 9 | 1.85-1.57 (m, 2H) |
| 10 | 1.57-1.32 (m, 2H) |
| 11 | 1.04-0.82 (m, 3H) |

Example 4

Synthesis of 2-[2-(3-butoxyphenyl)-ethylamino]-N,N-dimethylacetamide

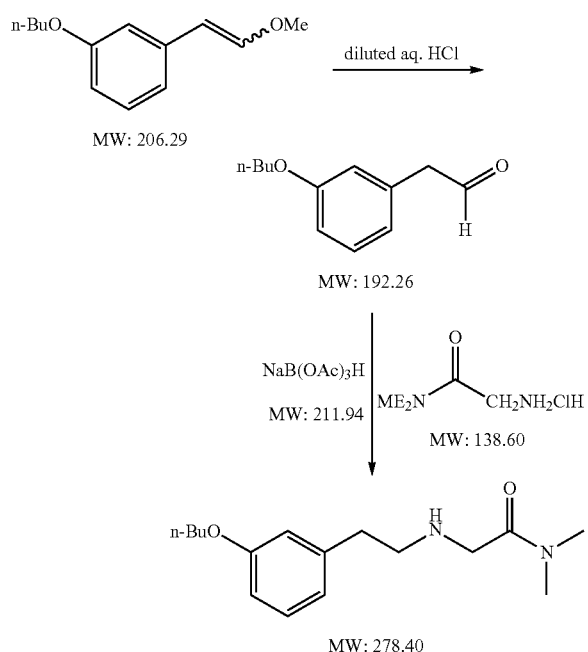

A solution of 1-butoxy-3-(2-methoxyvinyl)benzene; 20.7 kg (25.8 kg×80.2% assay, 100.3 mol; 1 equivalent), 2N aqueous hydrochloric acid (7.3 kg) and acetonitrile 278 kg was kept at about 0° C. until reaction completion (1-butoxy-3-(2-methoxyvinyl)benzene <3%). This was added to a mixture containing 2-amino-N,N-dimethylacetamide hydrochloride; 15.5 kg (16.6 kg×93.3% assay) (111.7 mol), water 6.2 kg and acetonitrile 93 kg at about 10° C., warmed to and held at 40° C. until reaction completion. The temperature of the batch was adjusted to about 0° C., and a solution of sodium triacetoxyborohydride 44.3 kg (99% assay, 207 mol) in acetonitrile 93 kg at about 5° C. After complete reaction (<2% residual quantity of 3-n-butoxy-phenylacetaldehyde), the batch was quenched with water 207 kg and the biphasic mixture was concentrated under vacuum at about 40° C. to about 90 L. The batch was diluted with methyl tert-butyl ether 104 kg and the layers were separated. The organic layer was washed with water twice (about 133 kg each time). The combined aqueous layers were extracted with methyl tert-butyl ether 104 kg, and the separated organic layer was washed with water 62 kg. The pH of the combined aqueous layers was adjusted to about 9 using 30% aqueous sodium hydroxide solution and extracted with methyl tert-butyl ether twice (104 kg each time). The combined organic layer was concentrated under vacuum, using a series of dilution with methyl tert-butyl ether (20 kg each time) and concentrated, to a final volume of about 20 L. The batch was further azeotropically dried by a series of dilution with methyl isobutyl ketone 25 kg and concentrated under vacuum to a final volume of 40 L, providing 2-[2-(3-butoxyphenyl)-ethylamino]-N,N-dimethylacetamide free base 20.1 kg (72.1 mol, 72% molar yield) as a concentrated solution in methyl isobutyl ketone. The identity of 2-[2-(3-butoxyphenyl)-ethylamino]-N,N-dimethylacetamide (free base) was consistent with MS (M+1=279.0), with 400 MHz $^1$H NMR and elemental analysis.

Example 5

Synthesis of 2-[2-(3-butoxyphenyl)-ethylamino]-N,N-dimethylacetamide 3-butoxyphenylacetaldehyde 1.95 g (1 equiv.) and 2-amino-N,N-dimethylacetamide 5.18 g (5 equiv.) were dissolved in anhydrous THF 340 mL. To this reaction mixture acetic acid 3.47 mL (6 equiv.) was added drop wise and the resulting solution was stirred for 5 minutes. To this solution STAB-H 8.6 g (4 equiv.) was added in portions and stirred for 2.5 hours. After the reaction was complete, Na$_2$CO$_3$ aqueous solution was added and the organic layer was separated. The aqueous layer was extracted twice with DCM 200 mL. The organic layers were combined, dried and concentrated. A flash column chromatography performed on crude material (8% ethyl acetate in heptanes) yielded 1.66 g (59% molar yield of 2-[2-(3-butoxyphenyl)-ethylamino]-N,N-dimethylacetamide free base).

Example 6

2-[2-(3-butoxyphenyl)-ethylamino]-N,N-dimethylacetamide hydrochloride

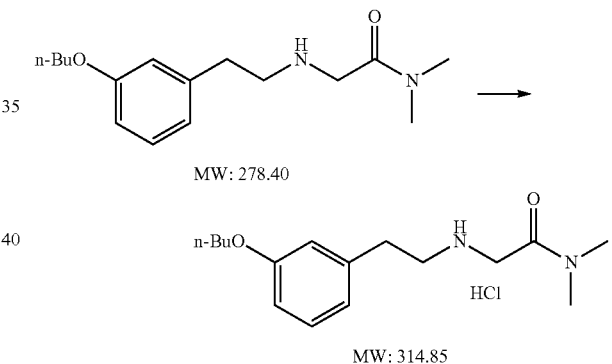

A solution containing gaseous hydrogen chloride (about 4 kg) in methyl tert-butyl ether (about 36 Kg) is added to a solution of 2-[2-(3-butoxyphenyl)-ethylamino]-N,N-dimethylacetamide free base 13.5 kg (48.5 mol) in methyl isobutyl ketone at about 25° C. The resulting suspension was filtered at about 0-5° C., and the filter cake was washed with cold methyl isobutyl ketone. The collected solid was suspended in methyl isobutyl ketone 68 kg at 35-40° C. for several hours, and then filtered at about 20° C. The filter cake was washed with methyl isobutyl ketone 14 kg. The collected solid was dissolved in a mixture of water 1.4 kg and methyl isobutyl ketone 54 kg and polished filtered. The filtrate was azeotropically dried, with a series of dilution with methyl isobutyl ketone and concentrated, to a final volume of about 81 L. The precipitated solids were filtered at 30-35° C. The collected solid was washed with methyl isobutyl ketone 14 kg, and then dried at about 40° C. under vacuum. The dried solid was sieved to provide 2-[2-(3-butoxyphenyl)-ethylamino]-N,N-dimethylacetamide hydrochloride 10.64 kg, (33.8 mol) in 69.7% molar yield. The identity of 2-[2-(3-butoxyphenyl)-ethylamino]-N,N-dimethylacetamide hydrochloride is confirmed by elemental analysis (theoretical vs found: C, 61.04% vs 61.3±0.2 wt %; H, 8.64% vs 8.7±0.1 wt %; N, 8.90% vs 8.9±0.1 wt %; O 10.16% vs 10.17±0.1 wt %; Cl 11.26% vs 10.2±0.5 wt %) (MS (M+1: 279.0), and 300 MHz $^1$H NMR Spectrum in DMSO Bruker Avance 300 at 20° C.:

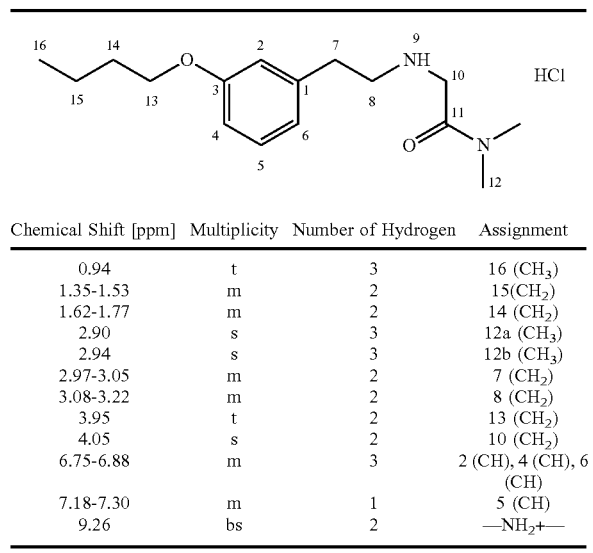

| Chemical Shift [ppm] | Multiplicity | Number of Hydrogen | Assignment |
|---|---|---|---|
| 0.94 | t | 3 | 16 ($CH_3$) |
| 1.35-1.53 | m | 2 | 15($CH_2$) |
| 1.62-1.77 | m | 2 | 14 ($CH_2$) |
| 2.90 | s | 3 | 12a ($CH_3$) |
| 2.94 | s | 3 | 12b ($CH_3$) |
| 2.97-3.05 | m | 2 | 7 ($CH_2$) |
| 3.08-3.22 | m | 2 | 8 ($CH_2$) |
| 3.95 | t | 2 | 13 ($CH_2$) |
| 4.05 | s | 2 | 10 ($CH_2$) |
| 6.75-6.88 | m | 3 | 2 (CH), 4 (CH), 6 (CH) |
| 7.18-7.30 | m | 1 | 5 (CH) |
| 9.26 | bs | 2 | —$NH_2$+— |

Bruker Avance 300 $^{13}$C-NMR Spectrum in DMSO at 20° C.

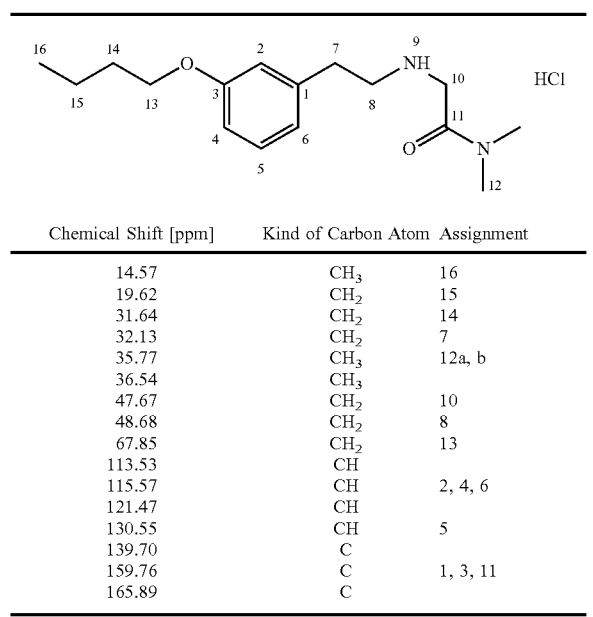

| Chemical Shift [ppm] | Kind of Carbon Atom | Assignment |
|---|---|---|
| 14.57 | $CH_3$ | 16 |
| 19.62 | $CH_2$ | 15 |
| 31.64 | $CH_2$ | 14 |
| 32.13 | $CH_2$ | 7 |
| 35.77 | $CH_3$ | 12a, b |
| 36.54 | $CH_3$ | |
| 47.67 | $CH_2$ | 10 |
| 48.68 | $CH_2$ | 8 |
| 67.85 | $CH_2$ | 13 |
| 113.53 | CH | |
| 115.57 | CH | 2, 4, 6 |
| 121.47 | CH | |
| 130.55 | CH | 5 |
| 139.70 | C | |
| 159.76 | C | 1, 3, 11 |
| 165.89 | C | |

Example 7

Synthesis of 2-[2-(3-butoxyphenyl)-ethylamino]-N,N-dimethylacetamide hydrochloride 2-[2-(3-butoxyphenyl)-ethylamino]-N,N-dimethylacetamide free base 8.10 g (29 mmol; 1 equiv.) grams was dissolved in diethyl ether 15 mL. To this solution HCl in ether solvent 46 mL (2 mmol) was added and vigorously stirred. The residue formed was scratched at 0° C. to produce a white precipitate of crude 2-[2-(3-butoxyphenyl)-ethylamino]-N,N-dimethylacetamide hydrochloride. This precipitate was further purified by trituration in ethyl acetate hydrochloride 40 mL 6.66 g (21.1 mmol; 72% yield).

Example 8

Synthesis of 2-[2-(3-butoxyphenyl)-ethylamino]-N,N-dimethylacetamide hydrochloride A solution of 2-[2-(3-butoxyphenyl)-ethylamino]-N,N-dimethylacetamide free base 5.4 Kg(19.40 mol) in methyl isobutyl ketone solution 35 L was added to 37% hydrochloric acid 2.03 kg. The mixture was dried azeotropically by repeated cycles of dilution with methyl isobutyl ketone and then concentrated under vacuum at <45° C. to about 27 L residual volume. The precipitated solid was filtered and was washed sequentially with methyl isobutyl ketone 10.95 kg and heptanes 18.70 kg. The wet product was dried at 40° C., to give 2-[2-(3-butoxyphenyl)-ethylamino]-N,N-dimethylacetamide hydrochloride 4.91 Kg (15.59 mol) as a white solid in 80.3% yield. Spectral data ($^1$H NMR) of the solid are consistent with the assigned structure of 2-[2-(3-butoxyphenyl)-ethylamino]-N,N-dimethylacetamide hydrochloride.

Example 9

Synthesis of 2-[2-(3-butoxy-3,3,4,4,4-$d_5$-phenyl)-ethylamino]-N,N-dimethylacetamide

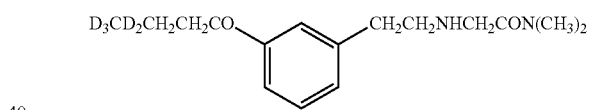

Phenylacetaldehyde-3-butoxy-3,3,4,4,4-$d_5$ 2 g (10.1 mmol; 1 equiv.) and 2-amino-N,N-dimethylacetamide 5.18 g (5 equiv.) were dissolved in anhydrous tetrahydrofuran 340 mL in an oven dried round ball flask. To this reaction mixture, acetic acid 3.47 mL (6 equiv.) was added drop wise and the resulting solution was stirred for 5 minutes. To this solution sodium triacetoxyborohydride (STAB-H) 8.6 g (4 equiv.) was added in portions and stirred for 2.5 hours. After the reaction was complete, sodium carbonate aqueous solution was added and the organic layer was separated. The aqueous layer was extracted twice with dichloromethane (200 mL). The organic layers were combined, dried and concentrated. A flash column chromatography performed on crude material (8% ethyl acetate in heptanes) yielded 1.7 g (6.0 mmol) of 2-[2-(3-butoxy-3,3,4,4,4-$d_5$-phenyl)-ethylamino]-N,N-dimethylacetamide (59.4% yield). $^1$H-NMR is reported in FIG. 1.

Phenylacetaldehyde-3-butoxy-3,3,4,4,4-$d_5$ used as starting material in the above synthesis was prepared according to the process reported in Example 1 or 2 starting from 3-hydroxybenzaldehyde by using 1-chlorobutane-3,3,4,4,4-$d_5$ instead of 1-chlorobutane and subsequent Wittig reaction.

Example 10

Synthesis of 2-[2-(3-butoxy-4,4,4,3,3-$d_5$-phenyl)-ethylamino]-N,N-dimethylacetamide hydrochloride

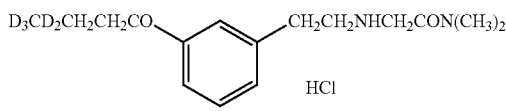

2-[2-(3-butoxy-4,4,4,3,3-$d_5$-phenyl)-ethylamino]-N,N-dimethylacetamide free base 8.25 g (29.1 mmol; 1 equiv.) was dissolved in diethylether 15 mL. To this solution a 2M HCl solution in diethylether (46 mL) was added and vigorously stirred. The gummy residue formed was scratched at 0° C. to produce a white precipitate of crude of 2-[2-(3-butoxy-3,3,4,4,4-$d_5$-phenyl)-ethylamino]-N,N-dimethylacetamide hydrochloride. This precipitate was further purified by trituration in ethyl acetate (40 mL). The resultant precipitate was filtered and dried under nitrogen to yield pure 2-[2-(3-butoxy-3,3,4,4,4-$d_5$-phenyl)-ethylamino]-N,N-dimethylacetamide hydrochloride 6.77 g (21.17 mmol, 73 yield).

$^1$H NMR-spectrum is reported in FIG. 1;
LC-MS:

| m/z | Abundance |
|---|---|
| 283.30 | 4.5 |
| 284.30 | 100.0 |
| 285.30 | 12.7 |
| 286.30 | 1.8 |
| 305.80 | 0.5 |
| 306.25 | 7.1 |
| 307.25 | 0.8 |

Example 11

Synthesis of 2-[2-(3-butoxyphenyl)-ethylamino]-N,N-dimethylacetamide hydrochloride A mixture of 1-butoxy-3-(2-methoxyvinyl)benzene; 20.7 kg (25.8 kg×80.2% assay, 100.3 mol=1 equivalent), 2N aqueous hydrochloric acid (7.3 kg) and acetonitrile 278 kg was kept at about 0° C. until reaction completion (1-butoxy-3-(2-methoxyvinyl)benzene <3%). This was added to a mixture containing 2-amino-N,N-dimethylacetamide hydrochloride (VI) (15.5 kg (16.6 kg×93.3% assay) (111.7 mol), water 6.2 kg and acetonitrile 93 kg at about 10° C., warmed to and held at 40° C. until reaction completion. The temperature of the batch was adjusted to about 0° C., and a solution of sodium triacetoxyborohydride 46.0 kg (99% assay, 215 mol) in acetonitrile 93 kg at about 5° C. was added. After complete reaction (<2% residual quantity of 3-n-butoxy-phenylacetaldehyde), the batch was quenched with water 207 kg and the biphasic mixture was concentrated under vacuum at about 40° C. to about 90 L. The batch was extracted with methyl tert-butyl ether (104 kg). The organic layer was washed with water twice (about 133 kg each time). The combined aqueous layers were extracted with methyl tert-butyl ether 104 kg, and the separated organic layer was washed with water 62 kg. The pH of the combined aqueous layers was adjusted to about 9 using 30% aqueous sodium hydroxide solution and extracted with methyl tert-butyl ether twice (104 kg each time). The combined organic layer was concentrated under vacuum, using a series of dilution with methyl tert-butyl ether (20 kg each time) and concentrated, to a final volume of about 20 L. The batch was further azeotropically dried by a series of dilution with methyl isobutyl ketone 25 kg and concentrated under vacuum to a final volume of 40 L, providing 2-[2-(3-butoxyphenyl)-ethylamine]-N,N-dimethylacetamide free base 20.1 kg (72.1 mol, 72% molar yield).

The solution was diluted to circa with methyl isobutyl ketone (130 L). The solution was added to 36% hydrochloric acid (7.6 kg). The mixture was dried azeotropically by repeated cycles of dilution with methyl isobutyl ketone and then concentrated under vacuum at <45° C. to about 100 L residual volume. The precipitated solid was filtered and was washed sequentially with methyl isobutyl ketone 40 kg and heptanes 70 kg. The wet product was dried at 40° C., to give 2-[2-(3-butoxyphenyl)-ethylamine]-N,N-dimethylacetamide hydrochloride 18.7 kg (59.4 mol) as a white solid in 82% yield from 2-[2-(3-butoxyphenyl)-ethylamine]-N,N-dimethylacetamide free base.

Example 12

Synthesis of 2-[2-(3-butoxyphenyl)-ethylamino]-N,N-dimethylacetamide hydrochloride 2-amino-N,N-dimethylacetamide hydrochloride; 15.5 kg (16.6 kg×93.3% assay) (111.7 mol), water 6.2 kg and acetonitrile 93 kg, was added at about 10° C. to a mixture of 1-butoxy-3-(2-methoxyvinyl)benzene; 20.7 kg (25.8 kg×80.2% assay, 100.3 mol=1 equivalent), 2N aqueous hydrochloric acid (7.3 kg) and acetonitrile 278 kg kept at about 0° C. until reaction completion (1-butoxy-3-(2-methoxyvinyl)benzene <3%). The thus obtained mixture was warmed to and held at 40° C. until reaction completion. The temperature of the stirred batch was adjusted to about 0° C. Acetonitrile 93 kg and sodium triacetoxyborohydride 44.3 kg (99% assay, 207 mol) were added to the stirred mixture kept at 5° C. After complete reaction (<2% residual quantity of 3-n-butoxy-phenylacetaldehyde), the batch was quenched with water 207 kg and the mixture was concentrated in vacuo under stirring at circa 40° C. to about 90 L. The batch was extracted with methyl tert-butyl ether (104 kg). The organic layer was washed with water twice (about 133 kg each time). The combined aqueous layers were extracted with methyl tert-butyl ether 104 kg, and the separated organic layer was washed with water 62 kg. The pH of the combined aqueous layers was adjusted to about 9 using 30% aqueous sodium hydroxide solution and extracted with methyl tert-butyl ether twice (104 kg each time). The combined organic layer was concentrated under vacuum, using a series of dilution with methyl tert-butyl ether (20 kg each time) and concentrated, to a final volume of about 20 L. The batch was further azeotropically dried by a series of dilution with methyl isobutyl ketone 25 kg and concentrated under vacuum to a final solution (40 L) of 2-[2-(3-butoxyphenyl)-ethylamine]-N,N-dimethylacetamide free base 20.1 kg (72.1 mol, 72% molar yield) which was diluted to circa 130 L with methyl isobutyl ketone and added with 37% hydrochloric acid (7.6 kg). The mixture was dried azeotropically by repeated cycles of dilution with methyl isobutyl ketone and then concentrated under vacuum at <45° C. to about 100 L residual volume. The precipitated solid was filtered and was washed sequentially with methyl isobutyl ketone 40 kg and heptanes 70 kg. The wet product was dried at 40° C., to give 2-[2-(3-butoxyphenyl)-ethylamino]-N,N-dimethylacetamide hydrochloride 19.0 kg (60.3 mol) as a white solid in 84% yield from 2-[2-(3-butoxyphenyl)-ethylamino]-N,N-dimethylacetamide free base.

Example 13

Synthesis of 2-[2-(3-butoxyphenyl)-ethylamino]-N,N-dimethylacetamide hydrochloride A solution of 1-butoxy-3-(2-methoxyvinyl)benzene; 20.7 Kg (25.8 kg×80.2% assay, 100.3 mol=1 equivalent), 2N aqueous hydrochloric acid (7.3 Kg) and acetonitrile 278 Kg was kept at about 0° C. until reaction completion (1-butoxy-3-(2-methoxyvinyl)benzene <3%). This was added to a mixture containing 2-amino-N,N-dimethylacetamide hydrochloride (VI) (111.7 mol), (readily prepared in situ from N-Boc-2-amino-N,N-dimethylacetamide and hydrochloric acid) water 6.2 Kg and acetonitrile 93 kg at about 10°.

The thus obtained mixture was warmed to and held at 40° C. until reaction completion. The temperature of the stirred batch was adjusted to about 0° C. Acetonitrile 93 kg and sodium triacetoxyborohydride 44.3 kg (99% assay, 207 mol.) were added to the stirred mixture kept at 5° C. After complete reaction (<2% residual quantity of 3-n-butoxy-phenylacetaldehyde), the batch was quenched with water 207 kg and the mixture was concentrated in vacuo under stirring at circa 40° C. to about 90 L. The batch was extracted with methyl tert-butyl ether (104 kg). The organic layer was washed with water twice (about 133 kg each time). The combined aqueous layers were extracted with methyl tert-butyl ether 104 kg, and the separated organic layer was washed with water 62 kg. The pH of the combined aqueous layers was adjusted to about 9 using 30% aqueous sodium hydroxide solution and extracted with methyl tert-butyl ether twice (104 kg each time). The combined organic layer was concentrated under vacuum, using a series of dilution with methyl tert-butyl ether (20 kg each time) and concentrated, to a final volume of about 20 L. The batch was further azeotropically dried by a series of dilution with methyl isobutyl ketone 25 kg and concentrated under vacuum to a final solution (40 L) of 2-[2-(3-butoxyphenyl)-ethylamino]-N,N-dimethylacetamide free base 19.1 kg (68.5 mol, 68.4% molar yield) which was diluted to circa 130 L with methyl isobutyl ketone and added with 37% hydrochloric acid (7.6 kg). The mixture was dried azeotropically by repeated cycles of dilution with methyl isobutyl ketone and then concentrated under vacuum at <45° C. to about 100 L residual volume. The precipitated solid was filtered and was washed sequentially with methyl isobutyl ketone 40 kg and heptanes 70 kg. The wet product was dried at 40° C., to give 2-[2-(3-butoxyphenyl)-ethylamino]-N,N-dimethylacetamide hydrochloride 18.2 kg (57.8 mol) as a white solid in 80% yield from 2-[2-(3-butoxyphenyl)-ethylamino]-N,N-dimethylacetamide free base.

Example 14

Synthesis of 1-butoxy-3-phenylacetaldehyde (V)

A solution consisting of 1-butoxy-3-(2-methoxyvinyl)benzene (200 mg, 0.001 mol), of HCl gas (0.001 mol) in THF (0.4 ml) and of acetonitrile (10V) was stirred at 25° C. for 30' to provide a solution of 1-butoxy-3-phenylacetaldehyde (V) in CH$_3$CN. The obtained solution was added to a mixture containing 2-amino-N,N-dimethylacetamide hydrochloride as per example 4.

Example 15

Synthesis of 1-butoxy-3-phenylacetaldehyde (V)

A solution consisting of 1-butoxy-3-(2-methoxyvinyl)benzene (200 mg, 0.001 mol), of HCl gas (0.001 mol., 1 equivalent) in EA (1 ml) and of CH$_3$CN (10V) was stirred at 0° C. for 30' to provide a solution of 1-butoxy-3-phenylacetaldehyde (V) in CH$_3$CN). The obtained solution was added to a mixture containing 2-amino-N,N-dimethylacetamide hydrochloride as per example 4.

Example 16

Synthesis of 1-butoxy-3-phenylacetaldehyde (V)

A solution consisting of 1-butoxy-3-(2-methoxyvinyl)benzene (206.29 g, 1 mol, 1 equivalent), of gas HCl (7.3 g, 0.2 equivalent) in MTBE (100 ml), H2O (18.0 g, 1 mol.) and of CH$_3$CN (10V) was stirred at 0-5° C. for 2 h to provide a solution of 1-butoxy-3-phenylacetaldehyde (V). The so obtained solution was added to a mixture containing 2-amino-N,N-dimethylacetamide hydrochloride as per example 4.

Example 17

Synthesis of 1-butoxy-3-phenylacetaldehyde (V)

A solution consisting of 1-butoxy-3-(2-methoxyvinyl)benzene (206.29 g, 1 mol., 1 equivalent), of 3N aqueous HCl (67 ml, 0.2 equivalent) and of CH3CN (10V) was stirred at 0-5° C. for 30' to provide a solution of 1-butoxy-3-phenylacetaldehyde (V). The obtained solution was added to a mixture containing 2-amino-N,N-dimethylacetamide hydrochloride as per example 4.

Example 18

Synthesis and isolation of 1-butoxy-3-phenylacetaldehyde (V)

A solution of 1-butoxy-3-(2-methoxyvinyl)benzene; 20.7 g, 2 N aqueous hydrochloric acid (7.3 g) and acetonitrile (278 g) was kept at about 0° C. until reaction completion (1-butoxy-3-(2-methoxyvinyl)benzene <3%). The reaction medium was made neutral by adding diluted sodium hydroxide. The batch was extracted with methyl tert-butyl ether and the solution was washed with water. Distillation of the solvent under reduced pressure provided 1-butoxy-3-phenylacetaldehyde (V) as residue.

The invention claimed is:

1. A process for preparing a compound of formula (I) or a pharmaceutically acceptable salt thereof:

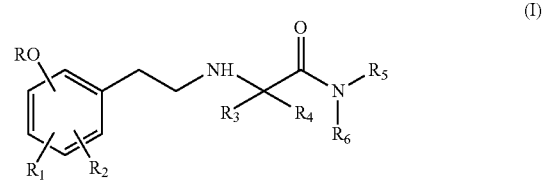

wherein R is $(C_3\text{-}C_{10})$alkyl, or $\omega$-trifluoro$(C_3\text{-}C_{10})$alkyl;

$R_1$ and $R_2$ are, independently, hydrogen, hydroxy, $(C_1\text{-}C_8)$alkoxy, $(C_1\text{-}C_8)$ alkylthio, halo, trifluoromethyl or 2,2,2-trifluoroethyl; or one of $R_1$ and $R_2$ is in ortho position to the R—O— group and, taken together with the same R—O—, represents a

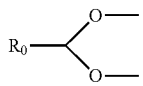

group where $R_0$ is $(C_2\text{-}C_9)$alkyl;

$R_3$ and $R_4$ are, independently, hydrogen, $(C_1\text{-}C_4)$alkyl; or $R_4$ is hydrogen and $R_5$ is a group selected from —CH$_2$—OH, —CH$_2$—O—$(C_1\text{-}C_6)$alkyl, —CH(CH$_3$)—OH, —(CH$_2$)$_2$—S—CH$_3$, benzyl and 4-hydroxybenzyl; or $R_4$ and $R_5$, taken together with the adjacent carbon atom, form a $(C_3\text{-}C_6)$cycloalkyl residue;

$R_5$ and $R_6$ are independently hydrogen or $(C_1\text{-}C_6)$alkyl; or taken together with the adjacent nitrogen atom form a 5-6 membered monocyclic saturated heterocycle, optionally containing one additional heteroatom chosen among —O—, —S— and —NR$_7$— where $R_7$ is hydrogen or $(C_1\text{-}C_6)$ alkyl;

and wherein optionally one or more hydrogen atom in the groups R, $R_1$, $R_2$, $R_3$, $R_4$, $R_5$ and $R_6$ can be substituted by a deuterium atom;

said process comprising the steps of:

a) reacting a compound of formula (II):

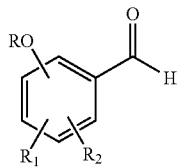

wherein R, $R_1$ and $R_2$ are as above defined with a compound of formula (III):

$$[(R_9)_3P\ CH_2OR_8]^+X^- \quad (III)$$

wherein $R_9$ is aryl or a (C1-C6) alkyl;

X is Cl, Br or I;

$R_8$ is $(C_1\text{-}C_6)$ alkyl or aryl; in the presence of a strong base to obtain a compound of formula (IV):

wherein R, $R_1$, $R_2$ and $R_8$ are as above defined and b) hydrolyzing the obtained compound of formula (IV) to obtain a compound of formula (V):

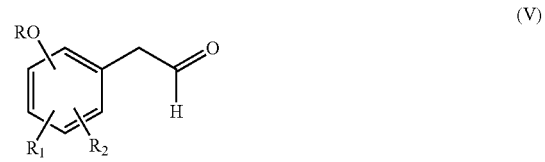

wherein R, $R_1$ and $R_2$ are as above defined and c) reacting the obtained compound of formula (V) with a compound of formula (VI) or a salt thereof:

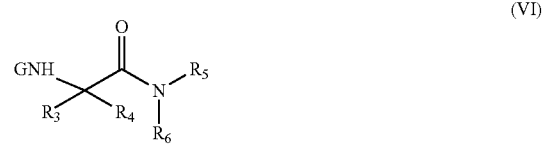

wherein $R_3$, $R_4$, $R_5$ and $R_6$ are as above defined and G is hydrogen or a protecting group of the amino group, to obtain a condensation compound;

d) reducing the obtained condensation compound to obtain the compound of formula (I)

or alternatively c') directly reacting the compound of formula (IV) as above defined with the compound of formula (VI) as above defined and reducing the obtained condensation compound to obtain the compound of formula (I); and e) optionally converting the obtained compound of formula (I) into a pharmaceutically acceptable salt thereof.

2. The process according to claim 1 for obtaining a compound of formula (I'):

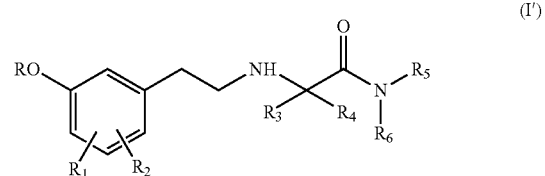

wherein R, $R_1$, $R_2$, $R_3$, $R_4$, $R_5$ and $R_6$ are as defined in claim 1.

3. The process according to claim 1 for obtaining a compound of formula (I) wherein:

R is $(C_4\text{-}C_6)$alkyl or CD$_3$-CD$_2$-$(C_2\text{-}C_4)$alkyl;

$R_1$ and $R_2$ are, independently, hydrogen or halo;

$R_3$ and $R_4$ are both hydrogen; and $R_5$ and $R_6$ are, independently, hydrogen or $(C_1\text{-}C_3)$alkyl.

4. The process according to claim 1 for obtaining a compound of formula (I) wherein R is n-butyl or CD$_3$-CD$_2$-CH$_2$—CH$_2$— and $R_1$, $R_2$, $R_3$, $R_4$, $R_5$ and $R_6$ are hydrogen.

5. The process according to claim 1 wherein the strong base of step a) is selected in the group consisting of alkyl lithium, lithium hexamethylsilazide, lithium isopropylamide and potassium tert-butoxide.

6. The process according to claim 5 wherein the strong base is lithium hexamethylsilazide.

7. The process according to claim 1, wherein the side product $(R_9)_3$ P formed in step a), wherein $R_9$ is as defined in claim 1, is oxidized to $(R_9)_3$ PO and removed.

8. The process according to claim 7 wherein (R9)3 PO is removed by filtration.

9. The process according to claim 7 wherein the obtained product (IV) is purified by chromatography.

10. The process according to claim 1, wherein the hydrolysis of step b) is carried out in aqueous acidic conditions.

11. The process according to claim 10 wherein the hydrolysis of step b) is carried out in acetonitrile and aqueous hydrochloric acid.

12. The process according to claim 1, wherein G in the compound of formula (VI) is hydrogen.

13. The process according to claim 1, wherein G in the compound of formula (VI) is a protecting group of the amino group selected from the group consisting of a carbamate N-carboxy alkyl group, N-t-butyl carbamate (BOC), N-benzyl carbamate (Cbz), bromobenzyl carbamate, p-chlorobenzylcarbamate and 9-fluorenylmethyl carbamate (Fmoc).

14. The process according to claim 1, wherein the reducing agent used in step d) is selected from the group consisting of sodium borohydride, sodium triacetoxyborohydride (STAB-H), Pd/$H_2$, and NaBH3CN.

15. The process according to claim 1, wherein the reducing agent used in step d) is sodium triacetoxyborohydride (STAB-H).

16. The process according to claim 1, wherein step b), step c) and step d) are carried out without isolating the intermediate products.

17. The process according to claim 16 wherein step b), step c) and step d) are carried out in acetonitrile and aqueous hydrochloric acid.

18. The process according to claim 1, wherein the pharmaceutically acceptable acid of step e) is selected from the group consisting of HCl, HBr, $CH_3SO_3H$, paratoluenesulfonic acid and phosphoric acid.

19. The process according to claim 1 wherein the compound of formula (II) wherein R, $R_1$ and $R_2$ are as defined in claim 1 is prepared by alkylation of a compound of formula (II) wherein R is hydrogen by reaction with a compound of formula RY wherein R is as defined in claim 1 and Y is a leaving group.

20. The process according to claim 19 wherein Y is selected from the group consisting of chloride, bromide, mesylate, para-toluenesulphonate, brosylate, nosylate and phosphate.

* * * * *